United States Patent
Takatsuka et al.

(10) Patent No.: US 7,476,216 B2
(45) Date of Patent: Jan. 13, 2009

(54) ELECTRIC SYRINGE FOR DENTAL ANESTHETIC

(75) Inventors: Minoru Takatsuka, Kita-Adachi-gun (JP); Tomio Nagashima, Kita-Adachi-gun (JP); Kazushi Konno, Kita-Adachi-gun (JP)

(73) Assignee: Nippon Shika Yakuhin Co., Ltd., Shimonoseki, Yamaguchi (JP)

( * ) Notice: Subject to any disclaimer, the term of this patent is extended or adjusted under 35 U.S.C. 154(b) by 135 days.

(21) Appl. No.: 10/676,327

(22) Filed: Sep. 30, 2003

(65) Prior Publication Data

US 2004/0073168 A1 Apr. 15, 2004

(30) Foreign Application Priority Data

Oct. 15, 2002 (JP) .............................. 2002-300353

(51) Int. Cl.
*A61M 37/00* (2006.01)
(52) U.S. Cl. .......................................... 604/131; 604/67
(58) Field of Classification Search ................. 604/131, 604/154, 65–67, 151; 433/32, 89–90, 103–105
See application file for complete search history.

(56) References Cited

U.S. PATENT DOCUMENTS

| | | |
|---|---|---|
| 2,702,547 A | 2/1955 | Glass |
| 3,395,704 A | 8/1968 | Frey et al. |
| 4,345,595 A | 8/1982 | Whitney et al. |
| 4,407,659 A | 10/1983 | Adam |
| 4,838,857 A | 6/1989 | Strowe et al. |
| 5,180,371 A | 1/1993 | Spinello |
| 5,681,286 A | 10/1997 | Niehoff |
| 5,690,618 A | 11/1997 | Smith et al. |
| 6,159,161 A * | 12/2000 | Hodosh ................... 600/561 |

| | | | |
|---|---|---|---|
| 2002/0077601 A1* | 6/2002 | Kawagishi et al. .......... 604/224 |
| 2004/0054328 A1* | 3/2004 | Langley et al. .............. 604/151 |

FOREIGN PATENT DOCUMENTS

EP   1 095 668 A1   5/2001

(Continued)

OTHER PUBLICATIONS

Patent Abstracts of Japan for JP07-213610 published on Aug. 15, 1995.

(Continued)

*Primary Examiner*—Nicholas D Lucchesi
*Assistant Examiner*—Theodore J Stigell
(74) *Attorney, Agent, or Firm*—Darby & Darby P.C.

(57) ABSTRACT

An electric syringe according to the invention injects a dental anesthetic by pressing a rubber plug of a cartridge filled with an anesthetic. The electric syringe includes: a push member configured to press and move the rubber plug of the cartridge; a drive motor configured to generate a drive force; a transmission mechanism part configured to transmit the drive force to the push member; and a control unit configured to control a moving of the push member by controlling the drive motor, wherein the control unit controls the drive motor to move the push member to gradually increase an injection speed of the anesthetic in the beginning of the injection and to move the push member to inject the anesthetic in a constant injection speed after a predetermined time has elapsed.

20 Claims, 8 Drawing Sheets

FOREIGN PATENT DOCUMENTS

| | | |
|---|---|---|
| EP | 1 186 311 A2 | 3/2002 |
| EP | 1 186 311 A3 | 9/2002 |
| JP | 3505286 | 11/1991 |
| JP | 07-213610 | 8/1995 |
| JP | 2530150 | 12/1996 |
| JP | 11500038 | 1/1999 |
| JP | 2001-070444 | 3/2001 |
| JP | 2002-191694 | 7/2002 |
| JP | 2002521149 | 7/2002 |
| RU | 2 012 359 C1 | 5/1994 |
| SU | 959792 | 9/1982 |
| WO | WO-0230490 | 4/2002 |
| WO | WO-02051476 | 7/2002 |

OTHER PUBLICATIONS

Patent Abstracts of Japan for JP2001-070444 published on Mar. 21, 2001.
Patent Abstracts of Japan for JP2002-191694 published on Jul. 9, 2002.
European Search Report for EP 03 02 1218 completed Jan. 11, 2006.
Partial European Search Report for EP 03 02 1218 completed Oct. 17, 2005.
English translation of Office Action for 2003129096/14(031097).

\* cited by examiner

ELECTRIC SYRINGE FOR DENTAL ANESTHETIC

BACKGROUND OF THE INVENTION

1. Field of the Invention

The present invention relates to an electric syringe for a dental anesthetic in which used when injecting an anesthetic in a dental treatment.

2. Description of the Related Art

As a generally used tool for injecting an anesthetic in a dental treatment, there is known a hand-operated syringe. When using the hand-operated syringe, since there is used an extremely fine needle for an anesthetic, there is required a large pushing force when injecting the anesthetic into the gum of a patient and thus there is required a great deal of labor to maintain a constant injection speed. In view of the above, there has been spread an electric syringe for a dental anesthetic (in which hereinafter referred to simply as an electric syringe) that aims at relieving a dental treatment load.

As a related art of such conventional electric syringe, there are known, for example, [An electric syringe for a dental treatment] disclosed in JP-A-7-213610, [An electric injection apparatus for a dental treatment] disclosed in JP-A-2001-70444, and [Mounting apparatus for a receiving cylinder in a cartridge-type injection apparatus for a dental treatment] disclosed in JP-A-2002-191694.

In the electric syringes disclosed in the documents, no consideration is given to the injection speed of the anesthetic; that is, a given quantity of anesthetic is output without controlling the injection speed. In a case where the injection of the anesthetic is started into the gum from such electric syringe, just after needling, a large quantity of anesthetic is injected, to thereby apply an excessively large pressure onto the tissue of the gum around a needlepoint of the needle, which makes a patient feel a pain.

Also, to start the injection of the anesthetic from the electric syringe, it is necessary to press down an operation button by an operator; however, when the operation button is operated in this manner, the vibrations of the operation transmits to the electric syringe and thus the needle is also moved, which also makes the patient feel a pain.

In the conventional electric syringes, the operation button is further requested so as to able to restrict the malfunction thereof.

Further, for the anesthetic, there presently exist two kinds of cartridges: that is, a cartridge for 1.0 ml and a cartridge for 1.8 ml. In the conventional electric syringes, the two kinds of cartridges are used by replacing cartridge holders that respectively hold their associated cartridges.

However, it is not desirable to use the cartridges while replacing a plurality of kinds of cartridge holders, because such usage results in the complicated management of the cartridge holders. Therefore, there have been demands for common use of the cartridge holders.

Also, there has been required a mechanism which is capable of mounting such cartridge holders simply.

SUMMARY OF THE INVENTION

It is therefore a first object of the invention is to provide an electric syringe that enhances the operation efficiency thereof without making a patient feel a pain and ease the pain of the patient.

Also, since the operation of the electric syringe is a medicine injection operation which must be executed carefully, there have been needs for avoiding positively such an operation which does not match the will of an operator (e.g. a dentist). Thus, it is therefore a second object of the invention to provide an electric syringe that prevents the malfunction thereof.

Further, it is a third object of the invention to provide an electric syringe which can use the 1.0 ml cartridge and 1.8 ml cartridge in common without replacing the cartridge holders and also in which, when the electric syringe is held at a set position, a rack for a push member is in contact with the rubber plug of the anesthetic at a constant pressure.

Still further, conventionally, there has been the need for a connecting mechanism which can use the 1.0 ml and 1.8 ml cartridges in common. Thus, it is a fourth object of the invention to provide an electric syringe which includes a cartridge holder connecting portion serving as a simple mechanism capable of strong connection of both of the 1.0 ml and 1.8 ml cartridges using a single cartridge holder.

To sum up, it is a main object of the invention to provide an electric syringe for a dental anesthetic which is enhanced in the whole operation efficiency thereof and can provide high reliability to both of a dentist and a patient.

In order to achieve the object, according to an aspect of the invention, there is provided an electronic syringe for injecting a dental anesthetic by pressing a rubber plug of a cartridge filled with an anesthetic, thereby injecting the anesthetic from a needlepoint of a dental needle connected to the cartridge, the electric syringe including: a push member configured to press and move the rubber plug of the cartridge; a drive motor configured to generate a drive force; a transmission mechanism part configured to transmit the drive force to the push member; and a control unit configured to control a moving of the push member by controlling the drive motor, wherein the control unit controls the drive motor to move the push member to gradually increase an injection speed of the anesthetic in the beginning of the injection and to move the push member to inject the anesthetic in a constant injection speed after a predetermined time has elapsed.

BRIEF DESCRIPTION OF THE DRAWINGS

The above objects and advantages of the present invention will become more apparent by describing in detail a preferred exemplary embodiment thereof with reference to the accompanying drawings, wherein.

DETAILED DESCRIPTION OF THE PREFERRED EMBODIMENTS

Figure 1:
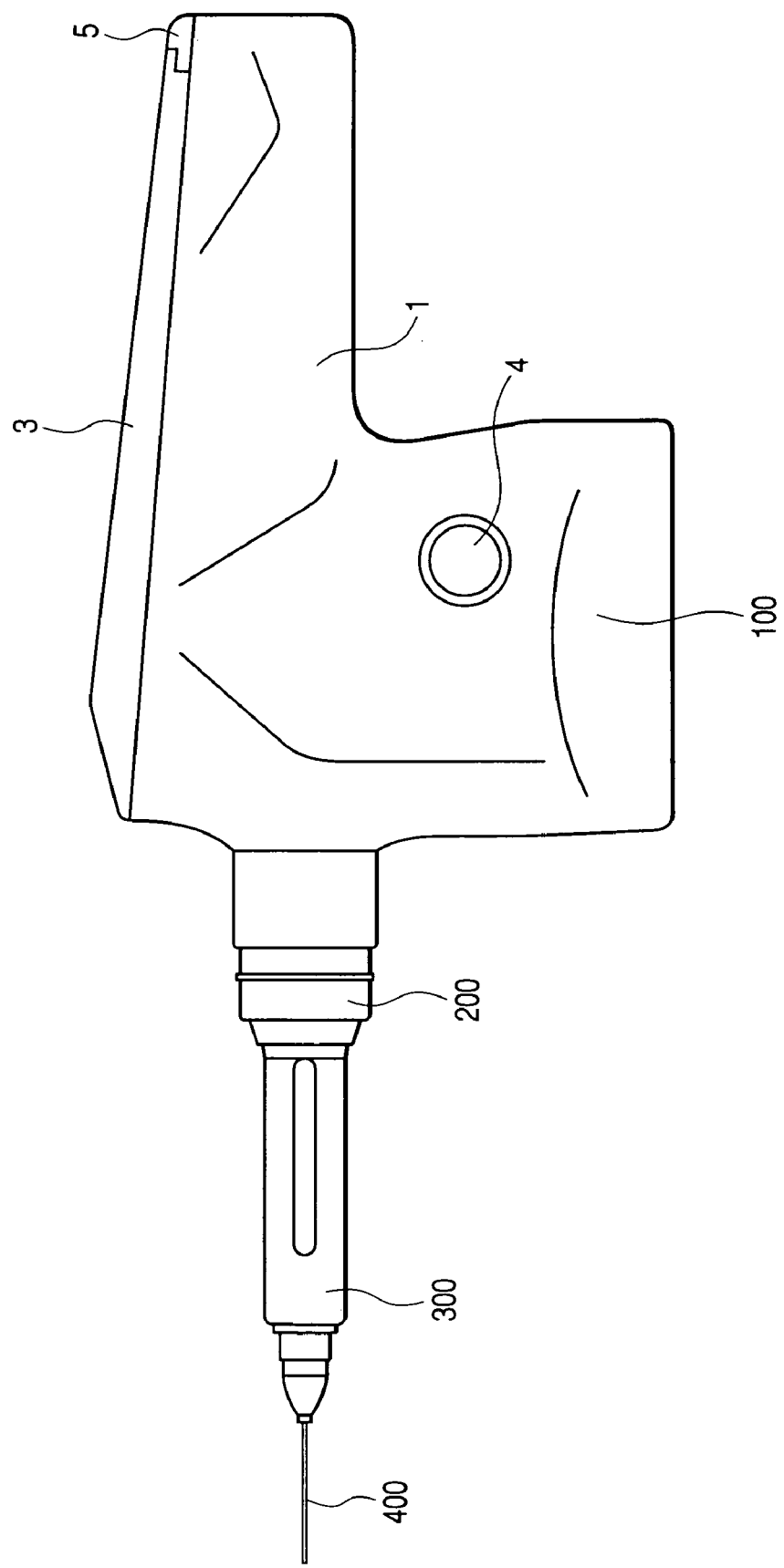
FIG. 1 is an external view of an electric syringe for a dental anesthetic according to the invention, explaining the outer appearance thereof.
Figure 2:
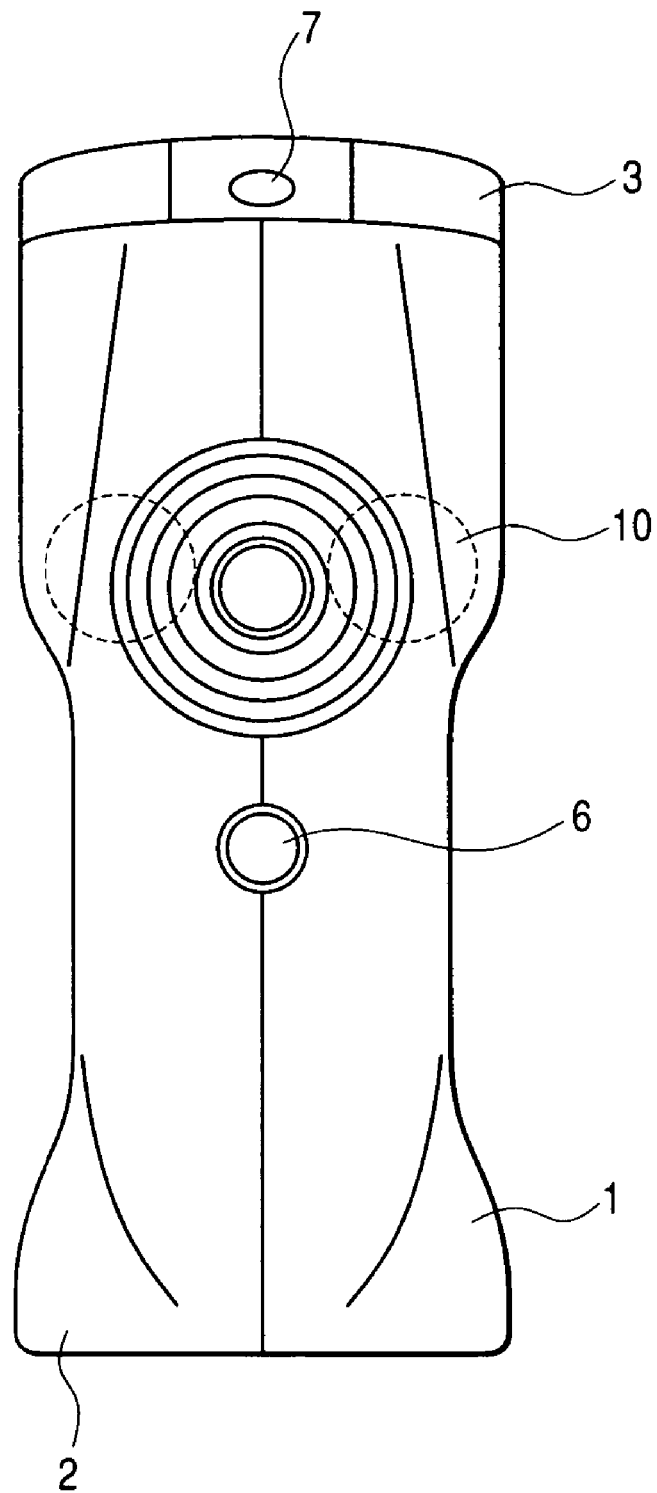
FIG. 2 is an external view of the electric syringe for a dental anesthetic, explaining the outer appearance thereof.
Figure 3:
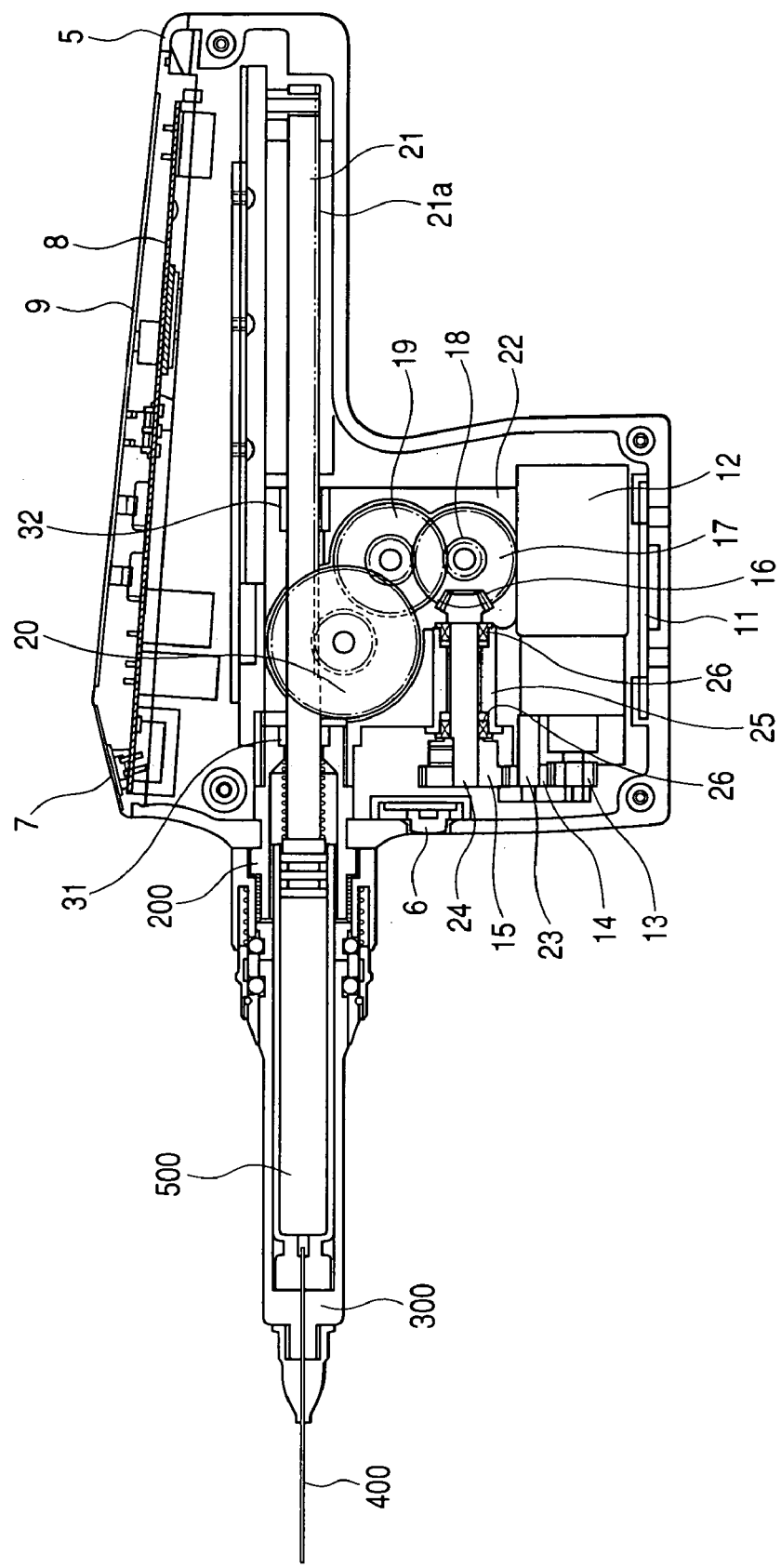
FIG. 3 is an internal mechanism view of the electric syringe for a dental anesthetic, explaining the internal structure thereof.
Figure 4:
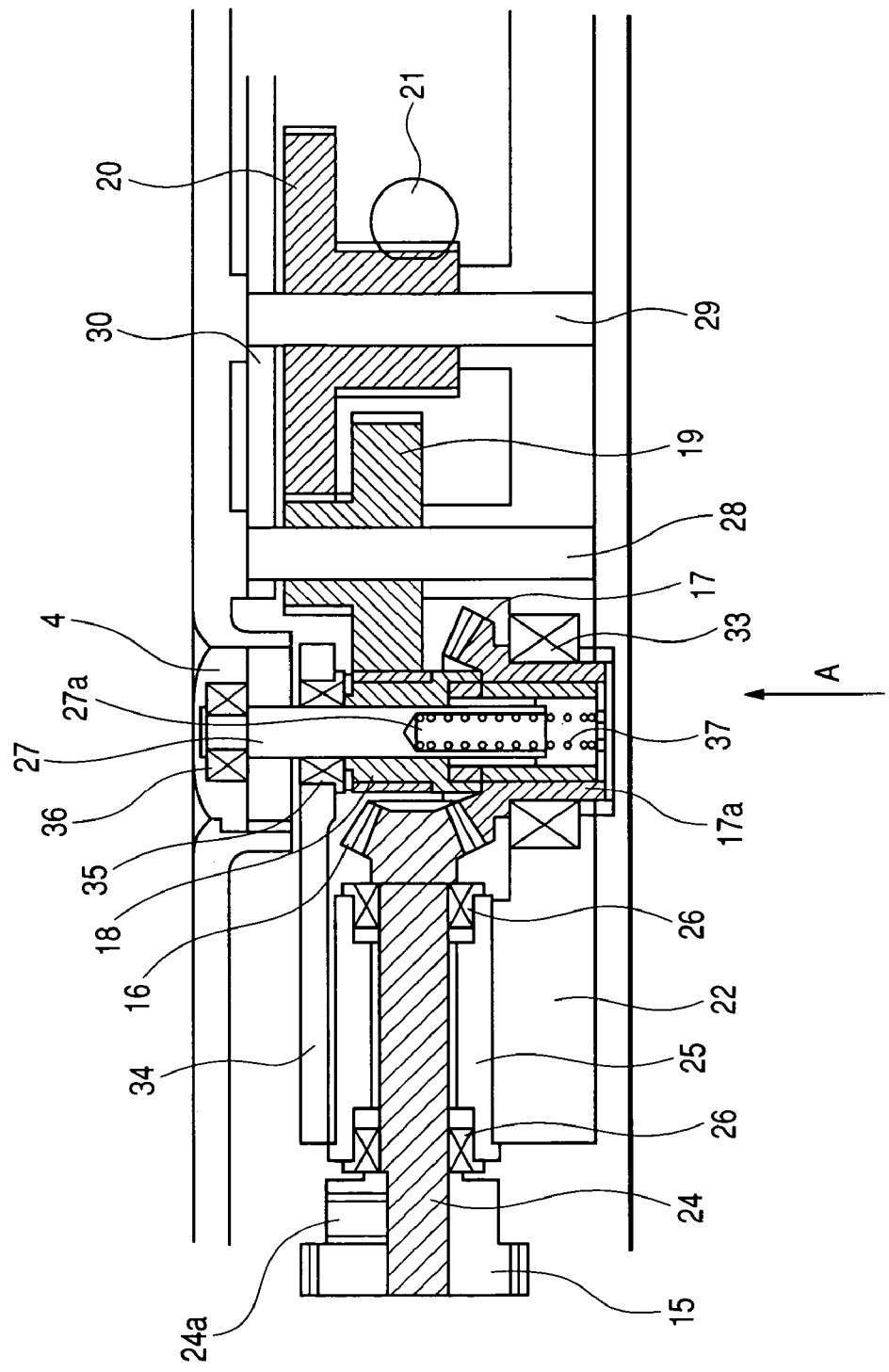
FIG. 4 is an internal mechanism view of the electric syringe for a dental anesthetic, explaining a clutch mechanism portion thereof.
Figure 5:
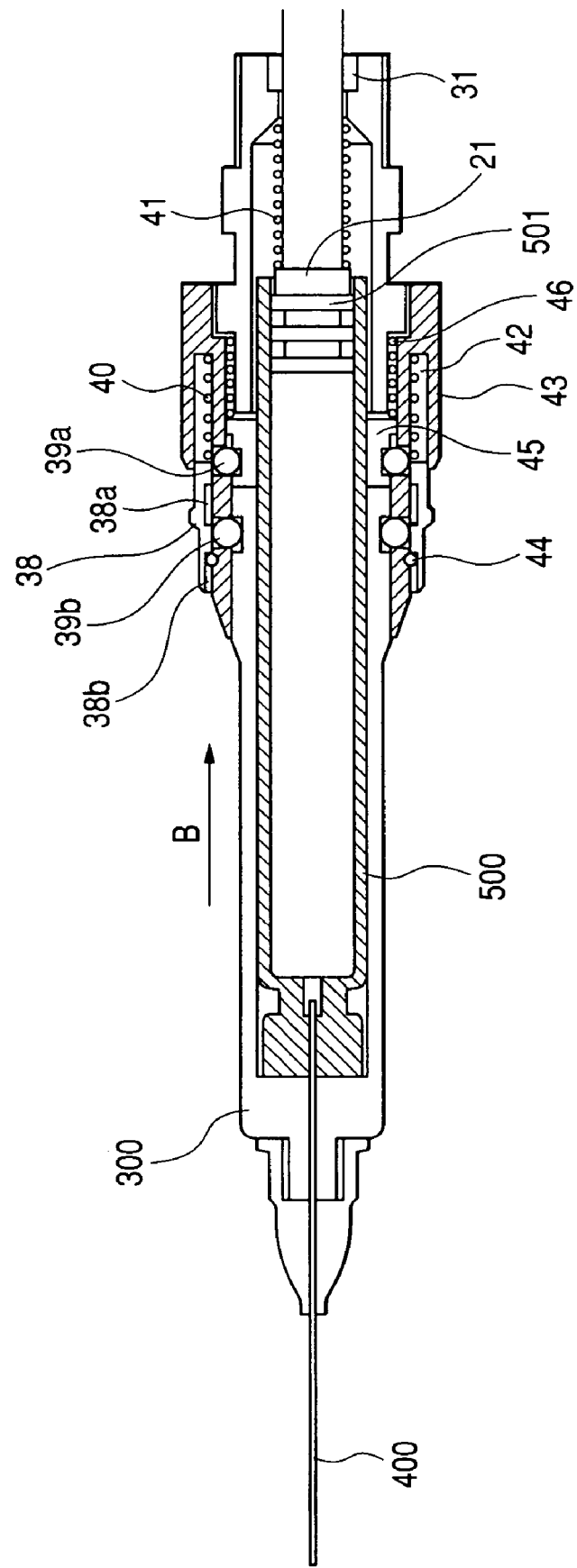
FIG. 5 is an internal mechanism view of the electric syringe for a dental anesthetic, explaining a cartridge holder connecting part thereof.

Hereinbelow, a preferred embodiment of an electric syringe for a dental anesthetic (in which hereinafter simply referred to as an electric syringe) according to the invention will be described with reference to the accompanying drawings. FIGS. 1 and 2 show external views of the electric syringe according to the embodiment, showing the outer appearance of the electric syringe; FIG. 3 shows an internal mechanism of the electric syringe, showing the interior structure thereof; FIG. 4 shows an internal mechanism of a clutch mechanism portion of the electric syringe; FIG. 5 shows an internal mechanism of a cartridge holder connecting part of the electric syringe; FIGS. 6 and 7 show explanatory views of the operation of the cartridge holder connecting part; and FIG. 8 shows an explanatory view of the injection speed control to be made in the electric syringe. Referring to the relation between FIGS. 1 and 2, when it is assumed that FIG. 2 is a front view of the electric syringe, FIG. 1 is a right side view of the electric syringe.

The electric syringe includes a main body part 100 (see FIGS. 1 and 2), a cartridge holder connecting part 200 (see FIGS. 1 and 3), a cartridge holder 300 (see FIGS. 1 and 3), a dental needle 400 (see FIGS. 1 and 3), and a cartridge 500 (see FIG. 3).

The main body part 100 is formed in such a manner as shown in FIG. 2: that is, two cover cases 1 and 2 are assembled together from right and left and a top plate 3 is then disposed on the assembled cover cases 1 and 2. In the main body part 100, as shown in FIG. 1, there are disposed a lock removing button 4 and an operation confirming lamp 5; and, as shown in FIG. 2, there are further disposed a safety sensor 6 as a first operation switch, and a start/stop sensor 7 as a second operation switch.

As shown in FIG. 3, on the top side of a control substrate 8, there is disposed an operation display part 9 with a display panel on which display and operation symbols are printed, and bonded to the front side thereof; and on the display panel of the operation display part 9, there are disposed a battery remaining amount display portion, a speed set display portion, a power supply switch, and a speed set switch.

The operation confirming lamp 5 receives supply power through the control substrate 8 and visually indicates an operation state of the electric syringe.

As shown in FIG. 2, two batteries 10 are set respectively on the two sides of the cover cases 1 and 2. Further, there is disposed a charging terminal (not shown) which belongs to a charging substrate 11 shown on the lower side of FIG. 3; and, in case where the main body part 100 is placed on a charger (not shown), the charging battery 10 is charged through the charging terminal. The charging battery 10 supplies supply power to various parts of the electric syringe as described later.

Next, description will be given below of the internal structure of the electric syringe.

Firstly, in the interior of the electric syringe, as shown in FIG. 3, there is disposed a drive motor 12.

The drive motor 12 is connected to a control drive circuit formed on the control substrate 8 and is configured in such a manner that the drive force thereof is controlled. Description will be given later of how the drive motor 12 is driven and controlled.

On the control substrate 8, there is also arranged a CPU (not shown) in which controls the whole operational status of the electric syringe. The CPU controls the drive circuit and a sound output unit, which will be described later. In the embodiment, the control substrate 8 (more specifically, the CPU and the control drive circuit arranged on the control substrate 8) corresponds to a control unit of the invention.

The drive motor 12 applies a drive force to a transmission mechanism part. On the main shaft of the drive motor 12, there is rotatably supported a spur gear 13.

The transmission mechanism part is a generic name of a gear train which is used to transmit the drive force given from the drive motor 12 through the spur gear 13; and includes an idler gear 14, a spur gear 15, a bevel gear 16, a bevel gear 17, a spur gear 18, a double gear 19, and another double gear 20.

The double gear 20 is configured to be engaged with a rack 21a of a push member 21 and thus the drive force is transmitted to the push member 21 through the transmission mechanism part.

The drive motor 12 and the transmission mechanism part are both stored in a gear case 22. The gear case 22 is held by and fixed to positioning bosses (each of which is formed so as to have a projecting shape) respectively disposed in the interior portions of the cases 1 and 2. Since the gear train is positioned with the gear case 22 as the reference thereof, the gear train is engaged with high accuracy to thereby be able to reduce generation of noises.

Next, description will be given below of the transmission operation of the transmission mechanism part.

The idler gear 14 is rotatably supported on a shaft 23 fixed to the gear case 22, and the idler gear 14 arranged so as to are engaged with the spur gear 13. The drive force is to be transmitted to the idler gear 14 from the spur gear 13.

The spur gear 15, as shown in FIGS. 3 and 4, is rotatably supported on and fixed to a rotary shaft 24 by a setscrew 24a. The rotary shaft 24 is supported on and fixed to the inner races of two bearings 26 whose outer races are held by a guide 25, and the rotary shaft 24 allowed to be rotated.

The spur gear 15 is engaged with the idler gear 14 and thus, to the spur gear 15, a drive force is transmitted from the idler gear 14. The drive force of the spur gear 15 is transmitted through the rotary shaft 24 to the bevel gear 16.

The bevel gear 16 is engaged with the bevel gear 17 and thus, to the bevel gear 17, a drive force is transmitted from the bevel gear 16. The transmitting direction of the drive force changes substantially by 90 degrees by the bevel gears 16 and 17.

A clutch shaft 27 is inserted through the bevel gear 17. The section of the clutch shaft 27 has such a structure as that of a spline shaft or a serrated shaft (in which hereinafter referred to as a sliding groove); and, the clutch shaft 27 is fitted into a sliding hole formed in the bevel gear 17 so as to be coincident with such sliding groove, and thus the clutch shaft 27 is slidably mounted.

The clutch shaft 27 is also inserted through the spur gear 18. In the spur gear 18 as well, there is formed a sliding hole which is coincident with the sliding groove of the clutch shaft 27. The clutch shaft 27 is fitted with the spur gear 18 coincident with such sliding groove and is thus slidably mounted.

The bevel gear 17 and spur gear 18 are formed as a double gear in appearance, while the bevel gear 17 corresponds to the large gear portion of the double gear and the spur gear 18 corresponds to the small gear portion thereof.

The drive force, which has been transmitted to the bevel gear 17, is then transmitted through the clutch shaft 27 to the spur gear 18.

The double gear 19 is rotatably supported on a shaft portion 28 as is shown in FIG. 4. The large gear portion of the double gear 19 is engaged with the spur gear 18, while the drive force of the spur gear 18 is transmitted to the double gear 19.

The double gear 20 is rotatably supported on a shaft portion 29 shown in FIG. 4. The large gear portion of the double gear 20 is engaged with the small gear portion of the double gear 19 and thus the drive force of the double gear 19 is transmitted to the double gear 20. The shaft portions 28 and 29 are respectively fixed by the gear case 22 and gear case cover 30.

The rack 21a formed in the push member 21 is further engaged with the small gear portion of the double gear 20, while the drive force is transmitted to the push member 21 through the rack 21a.

The moving direction of the push member 21 is restricted by bearing bushes 31 and 32 shown in FIG. 3 in such a manner that the push member 21 horizontally moves only in the right and left direction in FIG. 3. Due to the drive force transmitted to the rack 21a of the push member 21, the push member 21 is moved in the left direction so as to press against the rubber plug 501 (see FIG. 5) of a cartridge 500.

In the embodiment, a great deal of speed reduction is provided by the gear train of the transmission mechanism part and thus the push member 21 is moved more sufficiently slowly than the rotation of the drive motor 12, thereby being able to reduce the minimum unit of the anesthetic injection quantity.

The transmission mechanism part, as shown in FIG. 4, includes a clutch mechanism portion for releasing the transmission of the drive motor 12.

The clutch mechanism portion includes the bevel gear 17, spur gear 18, clutch shaft 27 and spring 37.

Since the sliding groove of the clutch shaft 27 is simply inserted through the sliding hole of the previously described bevel gear 17, the clutch shaft 27 is allowed to slide in the axial direction thereof. The bevel gear 17 is fixed to the inner race of a bearing 33 whose outer race is held by the gear case 22 in such a manner that the bevel gear 17 is allowed only to rotate.

The clutch shaft 27 is also slidably fixed to the inner race of a bearing 35 whose outer race is held by the gear case cover 34. Due to existence of the bearings 33 and 35, the clutch shaft 27 allowed to be freely rotated; and due to the mutual fitting engagement between the sliding groove and sliding hole, the bevel gear 17, spur gear 18 and clutch shaft 27 are allowed to rotate stably as an integral body.

Since the sliding groove of the clutch shaft 27 is fitted with the sliding hole of the bevel gear 17, the clutch shaft 27 allowed to slide upwardly and downwardly; and in particular, the clutch shaft 27 is allowed to slide along the sliding holes of the bevel gear 17 and spur gear 18.

On the clutch shaft 27, there is supported the lock removing button 4 through the bearing 36, while such consideration is given to the clutch shaft 27 that, even when the clutch shaft 27 is rotated, the lock removing button 4 is allowed surely to be prevented against rotation.

In the lower portion of the clutch shaft 27, a hole 27a is formed. In the bevel gear 17, a cylindrical-shaped tube portion 17a is formed. A spring 37 is disposed so as to extend over the hole 27a and tube portion 17a. Normally, the clutch shaft 27 is biased in direction represented by an arrow A in FIG. 4 and can be stabilized in a state where it is positioned on the upper side shown in FIG. 4.

In the case where the lock removing button 4 is situated on the upper side as in the embodiment, the sliding holes of the bevel gear 17 and spur gear 18 are both engaged with the sliding groove of the clutch shaft 27; and in a case where the drive force is transmitted to the bevel gear 17, the drive force is transmitted to the spur gear 18 through the clutch shaft 27. Normally, the sliding groove and sliding holes of the bevel gear 17, clutch shaft 27 and spur gear 18 are engaged with each other, so that the drive force generated due to rotation transmitted from the drive motor.

On the other hand, in a case where the lock removing button 4 is pressed down and is thereby positioned on the lower side (the state not shown), since the sliding groove of the clutch shaft 27 is engaged only with the sliding hole of the bevel gear 17 but is not engaged with the sliding hole of the spur gear 18, even when the drive force is transmitted to the bevel gear 17, the drive force is transmitted to the clutch shaft 27 but not to the spur gear 18, so that the drive force in the transmission mechanism part is released.

As described above, according to the transmission mechanism part of the embodiment, in a case where the lock removing button 4 is pressed down and thus the transmission of the transmission mechanism part is cut off by the clutch mechanism portion, the push member 21 can be pressed so as to be movable; and thus by releasing the lock removing button 4, the transmission of the transmission mechanism part is connected by the clutch mechanism portion.

Description will be given below of the cartridge holder connecting part 200.

The cartridge holder connecting part 200, as shown in FIG. 5, includes a mounting and removing ring 38, a first ball 39a, a second ball 39b, a mounting and removing ring biasing spring 40, a push member biasing spring 41, a spring storage portion 42, a connecting ring 43, a stopper 44, a ball pusher 45 and a ball pusher biasing spring 46.

Figure 6A:
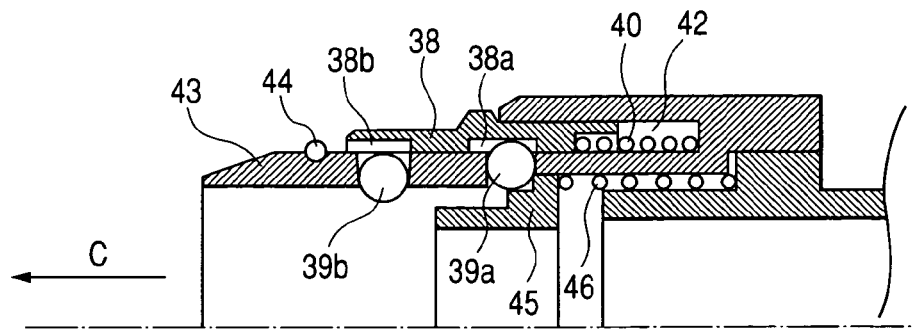
FIGS. 6A through 6D are explanatory views of the operation of the cartridge holder connecting part.

Next, description will be given below in more detail of the above mechanisms as well as the above mounting and removing operations with reference to FIGS. 6A through 6D and FIGS. 7A through 7D. Firstly, FIG. 6A shows the state of the cartridge holder connecting part 200 in which the cartridge holder 300 is not connected yet. As shown in FIG. 6A, the connecting ring 43 is configured so as to store the first ball 39a and second ball 39b therein. The connecting ring 43 is configured to prevent the second ball 39b from moving into the tube portion of the connecting ring 43 (for example, by forming the positioning hole of the second ball 39b in a truncated cone shape).

The ball pusher 45 is biased in direction represented by an arrow C in FIG. 6A due to the biasing force of the ball pusher biasing spring 46. The ball pusher 45 is formed as a cylindrical body having a multi-stage-shaped outer peripheral surface and, in more detail, as shown in FIG. 6A, the ball pusher 45 includes two kinds of stage portions, that is, a lower stage portion having a small diameter and an upper stage portion having a large diameter.

Similarly, the mounting and removing ring 38 is biased in direction represented by an arrow C in FIG. 6A due to the biasing force of the mounting and removing ring biasing spring 40 which is to be stored in the spring storage portion 42 of the connecting ring 43. The mounting and removing ring 38 is formed as a cylindrical body having an inner peripheral surface with a groove and, in more detail, the ring 38 includes two groove portions 38a and 38b.

In the state shown in FIG. 6A, the first ball 39a in contact with the upper stage portion of the multi-stage-shaped outer peripheral surface of the ball pusher 45 moves into the groove portion 38a of the mounting and removing ring 38, and the mounting and removing ring 38 is pressed in the arrow mark c direction by the mounting and removing ring biasing spring 40; and the ball pusher 45 is also pressed in direction of the arrow C by the ball pusher biasing spring 46, so that the mounting and removing ring 38 and first ball 39*a* are both positively restricted in the movements thereof.

Figure 6B:
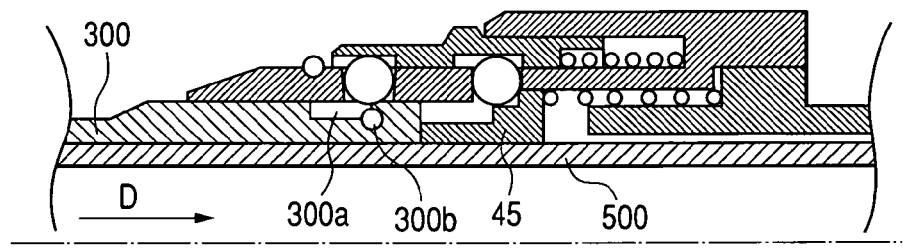

Now, it is assumed that, as shown in FIG. 6B, the cartridge holder 300 with the cartridge 500 for 1.0 ml or 1.8 ml of the anesthetic previously incorporated therein is inserted into the above cartridge holder connecting part 200 in direction represented by an arrow D in FIG. 6B (in direction of arrow B in FIG. 5) and reaches a position where it can be contacted with the ball pusher 45 (FIG. 6B shows the above state).

The cartridge holder 300 includes an outer peripheral surface with a groove in which a circular-ring-shaped groove portion 300*a* is formed. In the groove portion 300*a*, there is stored a ring-shaped step portion 300*b*.

Figure 6C:
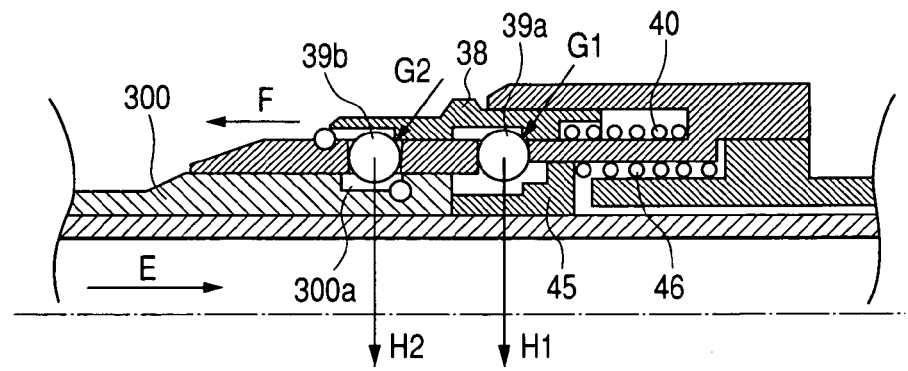

As shown in FIG. 6C, in a case where the cartridge 300 is further inserted in direction represented by an arrow E in FIG. 6C, the ball pusher 45 is also pressed and moved in direction of the arrow E against the biasing force of the ball pusher biasing spring 46. Due to the above, between the first ball 39*a* and the multi-state-shaped outer peripheral surface of the ball pusher 45, there is generated such clearance that allows the first ball 39*a* to move; the groove portion 300*a* is situated just below the second ball 39*b*; and the mounting and removing ring 38 biased in direction represented by an arrow F in FIG. 6C by the mounting and removing ring biasing spring 40 is pressed against the first ball 39*a* in direction represented by an arrow G1 in FIG. 6C. Therefore, the first ball 39*a* is moved in direction represented by an arrow H1 in FIG. 6C. And, since the mounting and removing ring 38 is pressed against the second ball 39*b* in direction represented by an arrow G2, the second ball 39*b* is moved in direction represented by an arrow H2.

Figure 6D:
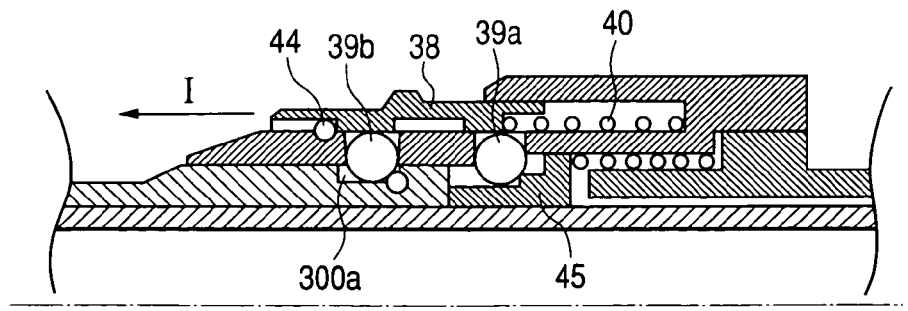

As shown in FIG. 6D, the mounting and removing ring 38 moves further in direction represented by an arrow I, while the mounting and removing ring 38 is contacted with the stopper 44 and thus the movement of the ring 38 is restricted, so that the mounting and removing ring 38 is stabilized in such a state as shown in FIG. 6D. In the stabilization, because mechanical sounds are generated, the operator confirms that the cartridge holder 300 has been connected.

After completion of the connection of the cartridge holder 300, the first ball 39*a* is contacted with the mounting and removing ring 38 and he lower stage portion of the multi-stage-shaped outer peripheral surface of the ball pusher 45 and also the second ball 39*b* is contacted with the mounting and removing ring 38 and groove portion 300*a*, whereby the cartridge holder 300 can be firmly fixed to the cartridge holder connecting part 200.

In the case where the cartridge 500 and cartridge holder 300 are inserted into the cartridge connecting part 200 as described above, the cartridge 500 and the cartridge holder 300 are automatically fixed to the electric syringe. Therefore, it is quite easy to mount the cartridge 500 and the cartridge holder 300.

Figure 7A:
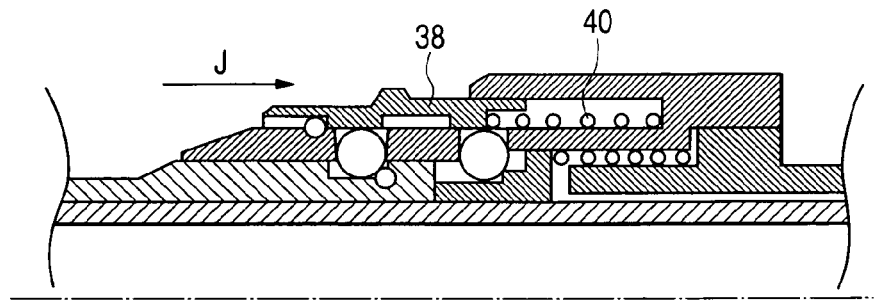
FIGS. 7A through 7D are explanatory views of the operation of the cartridge holder connecting part.
Figure 8:
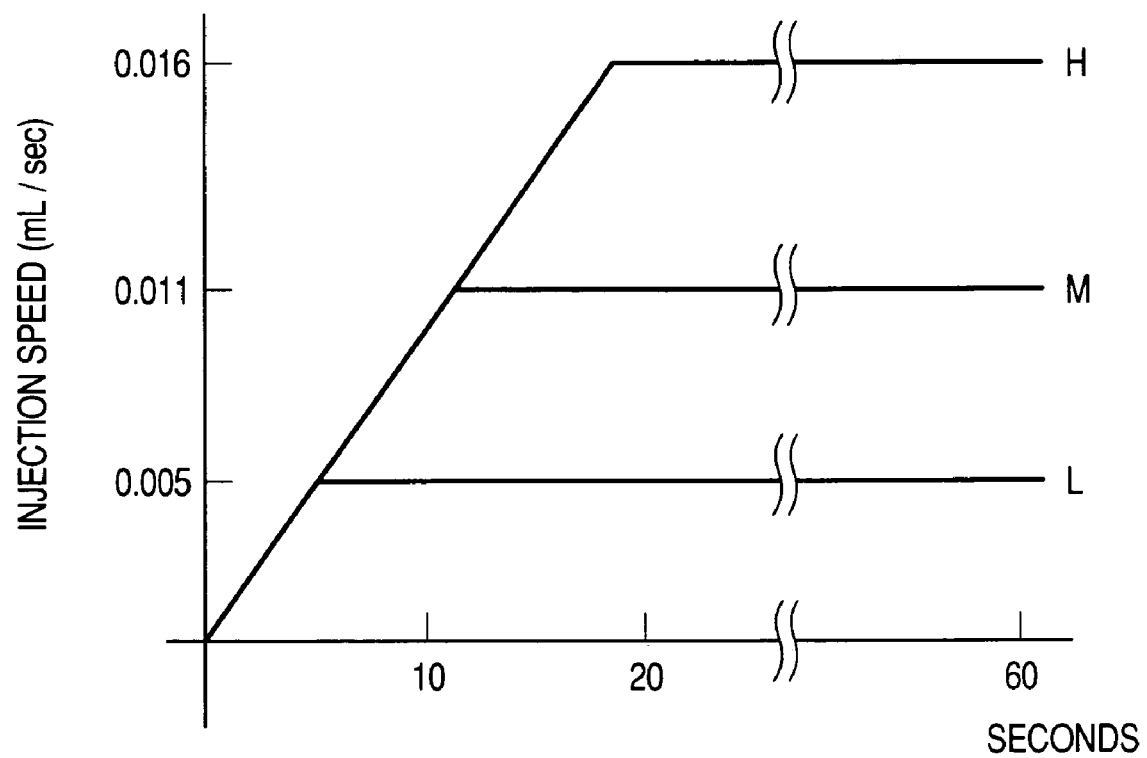
FIG. 8 is an explanatory view of the injection speed control to be made in the invention.

When pulling out and remove the cartridge 500 and cartridge holder 300 from the cartridge holder connecting part 200, as shown in FIG. 7A, the operator may move the mounting and removing ring 38 in direction represented by an arrow J against the biasing force of the mounting and removing ring biasing spring 40.

Figure 7B:
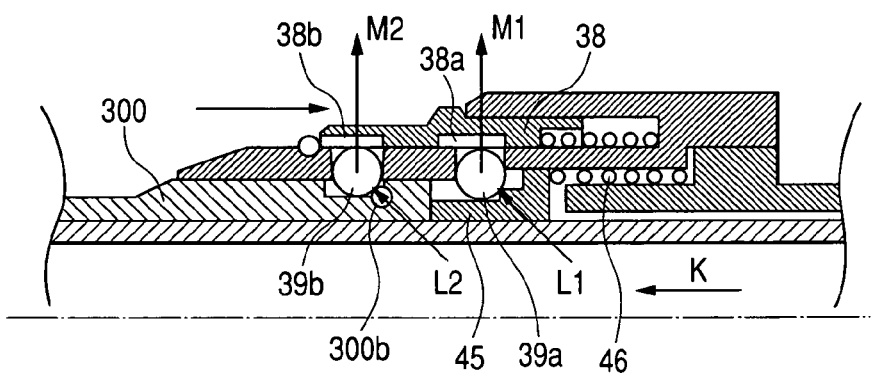

In a case where the mounting and removing ring 38 is further pushed and is thereby finally moved up to a state shown in FIG. 7B, the groove portion 38*a* can be situated just above the first ball 39*a* and the groove portion 38*b* can be situated just above the second ball 39*b*. Then, the ball pusher 45 and cartridge holder 300 are both biased in direction represented by an arrow K by the ball pusher biasing spring 46. In the above state, since the ball pusher 45 pushes the first ball 39*a* in direction represented by an arrow L1, the first ball 39*a* is moved in direction represented by an arrow M1; and also, because the step portion 300*b* of the cartridge holder 300 pushes the second ball 39*b* in direction represented by an arrow L2, the second ball 39*b* is moved in direction represented by an arrow M2.

Figure 7C:
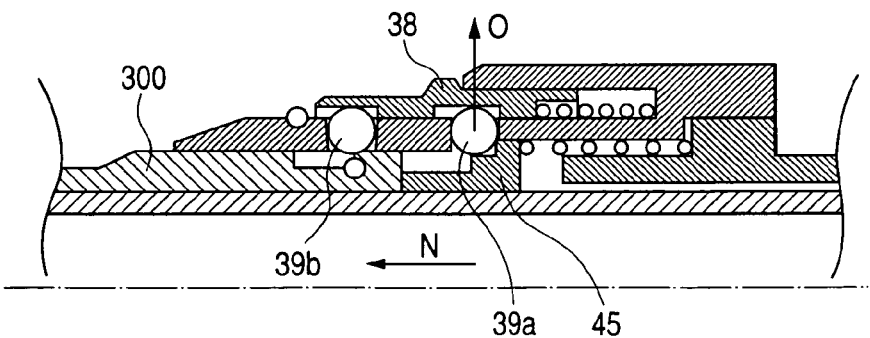

As shown in FIG. 7C, in a case where the ball pusher 45 is moved still further in direction represented by an arrow N to thereby push up the first ball 39*a* in direction represented by an arrow O, the movement of the mounting and removing ring 38 is also restricted by the first ball 39*a*; and further, in a state where the ball pusher 45 is pressed against the first ball 39*a*, in case where the first ball 39*a* is contacted with the upper stage of the multi-stage-shaped outer peripheral surface of the ball pusher 45, the movement of the mounting and removing ring 38 is stopped. In the state above, the cartridge 500 and cartridge holder 300 can be freely pulled out from the cartridge holder connecting part 200.

Figure 7D:
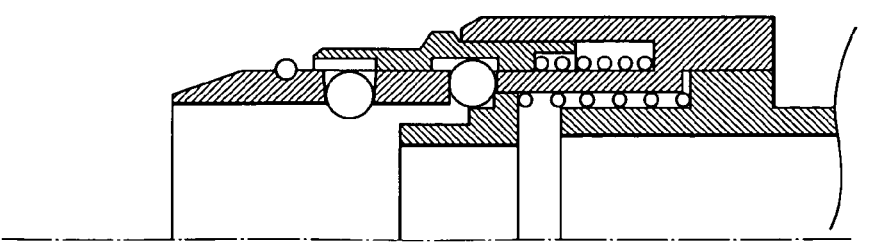

Finally, the cartridge holder 300 is removed, which provides such a state as shown in FIG. 7D. The state shown in FIG. 7D is the same as the state shown in FIG. 7A.

That is, the mounting and removing operations of the cartridge 500 and cartridge holder 300 with respect to the cartridge holder connecting part 200 are carried out in the above described manner.

Incidentally, the cartridge 500 includes two kinds of cartridges differing in length: that is, one cartridge for 1.0 ml of the anesthetic, the other for 1.8 ml of the anesthetic. In either of the two kinds of cartridges, when mounting the cartridge 500, in a case where the cartridge 500 is mounted in a state where the lock removing button 4 is pressed down to thereby allow the push member 21 to move, the push member 21 can be moved on by the push member biasing spring 41 while maintaining its contact with the rubber plug 501, and finally the mounting of the cartridge 500 is completed in a state where the push member 21 is contacted with the rubber plug 501 at a constant pressure, thereby being able to use either of the two kinds of cartridge 500 regardless of the lengths thereof.

Thus, it is possible to use the two kinds of cartridges for 1.0 ml and 1.8 ml of the anesthetic that are different in length from each other.

Next, description will be given below of the operation of the thus-structured electric syringe.

Firstly, the operator takes up the electric syringe that is placed on a charger (not shown) and presses down the power supply switch of the operation display part 9 to thereby turn on the power. Then, on the battery remaining amount display of the operation display part 9, an indication is shown that the charge is completed or not.

The electric syringe is configured to select one of an injection speed from among a plurality of the injection speed as shown in FIG. 8 (FIG. 8 shows three injection speeds that are configured to be selectable).

The operator may press down the speed set switch of the operation display part 9 and, while confirming the speed set display, may select the desired one of the injection speeds.

Next, of the two kinds of cartridges for 1.0 ml of anesthetic and for 1.8 ml of anesthetic that are different in the length, either one cartridge 500 is mounted onto the cartridge holder 300.

When setting the cartridge holder 300 onto the electric syringe, the lock removing button 4 is pressed down and the transmission of the transmission mechanism part is cut off by the clutch mechanism part; and in this state, the push member 21 is pushed and moved into the cartridge holder connecting part 200.

Further, in a state where the lock removing button 4 is pressed down and the transmission of the transmission mechanism part is cut off, the cartridge holder 300 is mounted. In the mounting, as shown in FIG. 5, when the push member 21 in contact with the rubber plug 501 of the cartridge 500 is pushed and moved toward the main body part 100 side, while the contact state of the push member 21 at a constant pressure is maintained due to the spring force of the push member biasing spring 41, the push member 21 is finally moved to its start position.

Then, the aforementioned operation is carried out to fix the cartridge holder 300 to the cartridge holder connecting part 200, thereby providing such a state as shown in FIG. 5. Then, the dental needle 400 is mounted, which can complete the initial operation for the operation of the electric syringe.

Next, in a case where the electric syringe is gripped by hand, the window hole portion of the safety sensor 6, which is a sensor of a light reflection type, is closed by the gripping hand and an input for operation of the sensor 6 is thereby enforced. And, in the above state, the window hole portion of the start/stop sensor 7, which is also a sensor of a light reflection type, is closed with a forefinger to thereby enforce the operation input thereof. In this manner, only when the safety sensor 6 and start/stop sensor 7 are both closed and operated, the control substrate 8 is allowed to control the drive motor 12 so as to start the anesthetic injection operation; and therefore, even in a case where only one of the two sensors is closed in error, the electric syringe can be surely prevented against the malfunction thereof.

Since the safety sensor 6 and start/stop sensor 7 are both a sensor of a light reflection type and are structured such that the window hole portions thereof are only closed, the electric syringe can be prevented against movement, which can in turn reduce the undesirable slight movement of a needlepoint of the needle which causes a pain in the patient.

The electric syringe is operated in this manner and, to release the air existing in the needle, while allowing the anesthetic to reach the needlepoint of the dental needle 400, the operation of the electric syringe is confirmed.

Next, the dental needle 400 is stuck into the gum of the patient and the start/stop sensor 7 is closed to thereby start the injection. During the injection, the sound output unit arranged on the control substrate 8 outputs a buzzing sound or a melodic sound. Such buzzing sound or a melodic sound not only can inform that the anesthetic is under injection but also can relieve the patient from anxiety.

Also, the control substrate 8, as shown in FIG. 8, drives the drive motor 12 to thereby control the moving amount of the push member 21 through the transmission mechanism part so that the injection can be started at a low injection speed so as to be able to provide a very small anesthetic injection quantity in the beginning of the injection, the injection speed can be increased substantially at a given variation rate and, after the passage of a given period, the injection speed can provide a constant speed.

In a case where the injection speed is set low in the beginning of the injection, a pain, which is felt by the patient in the beginning of the injection, can be reduced and thus the patient can be relieved from anxiety.

After injection of a given quantity of anesthetic, the forefinger, which is closing the start/stop sensor 7, is moved, thereby completing the injection operation.

That is, the electric syringe is operated in the above-mentioned manner.

According to the invention, the injection speed is controlled in such a manner that the injection quantity in the beginning of the injection can be set small; there is given such consideration that the patient can be relieved from anxiety due to generation of a buzzing sound or a melodic sound; and, the slight movement of the needlepoint of the needle in the injection operation can be prevented. Due to the above, there can be provided an electric syringe that is enhanced in the operation performance thereof so as to be able to prevent the patient from feeling a pain in the injection operation.

Also, since the injection operation can be executed only when the safety sensor and start/stop sensor are both operated, as in a sensor of a light reflection type, it is possible to use a switch which can be operated easily only by closing (shielding) the portion in which the sensor is disposed. According to the above configuration, there can realize not only the prevention of the malfunction of the electric syringe but also the enhancement in the operation performance thereof.

Further, according to the invention, there can be provided an electric syringe structured in the following manner: that is, provision of a clutch mechanism portion enables the clutch operation of a transmission mechanism part, which makes it possible to move a push member; by biasing the push member using a push member biasing spring, a cartridge for 1.0 ml and a cartridge for 1.8 ml can be used in common without replacing a cartridge holder; and, at a set position, a rack for the push member can be contacted with a rubber plug for an anesthetic at a constant pressure.

In addition, in the case of the connection with respect to the cartridge holder connecting part, the connection can be carried out automatically simply by inserting the cartridge holder with the cartridge assembled thereto into the cartridge holder connecting part, the present electric syringe is easy to handle.

To sum up, according to the invention, generally, there can be provided an electric syringe for a dental anesthetic that is enhanced in the operation performance as a whole and is thereby improved in the reliability for both of a dentist and a patient.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. An electric syringe for injecting a dental anesthetic by pressing a rubber plug of a cartridge filled with an anesthetic, thereby injecting the anesthetic from a needlepoint of a dental needle connected to the cartridge, the electric syringe comprising:

a push member configured to press and move the rubber plug of the cartridge;

a drive motor configured to generate a drive force;

a transmission mechanism part configured to transmit the drive force to the push member;

an operation switch having a window hole portion and a sensor of a light reflection type which detects whether or not the window hole portion is closed; and a control unit configured to control a moving of the push member by controlling the drive motor;

wherein the control unit starts the injection of the anesthetic when the sensor of the operation switch detects that the window hole portion is closed and controls the drive motor to move the push member to linearly increase an injection speed of the anesthetic at a constant, predetermined rate at the beginning of the injection and until reaching a selected injection speed, and then to move the push member to inject the anesthetic at the selected injection speed without further increase.

2. The electric syringe as claimed in claim 1 further comprising a sound output unit configured to output a sound,
wherein the control unit controls the sound output unit to output the sound during the injection of the anesthetic.

3. The electric syringe as claimed in claim 1, wherein the operation switch comprises:
a first operation switch having a first window hole portion configured to be closed by a hand gripping the electric syringe, and a first sensor of a light reflection type in which detects whether or not the first window hole portion is closed; and
a second operation switch having a second window hole portion configured to be closed by a finger, and a second sensor of a light reflection type in which detects whether or not the second window hole portion is closed, and
wherein the control unit starts the injection of the anesthetic when both of the first and the second window hole portions are detected by the first and the second sensor to be closed.

4. The electric syringe as claimed in claim 1, wherein the transmission mechanism part comprises:
a lock removing button arranged on a cover case of the electric syringe; and
a clutch mechanism portion configured to release the transmission of the drive force when the lock removing button is operated.

5. The electric syringe as claimed in claim 4 further comprising:
a cartridge holder connecting part; and
a cartridge holder configured to hold the cartridge and configured to be connectable to the cartridge holder connecting part.

6. The electric syringe as claimed in claim 5, wherein the cartridge holder is configured to hold each one of a plurality of cartridges having different lengths, and configured to be connectable to the cartridge holder connecting part.

7. The electric syringe as claimed in claim 6, wherein the cartridge holder is configured to hold each one of a first cartridge filled with 1.0 ml of the anesthetic and a second cartridge filled with 1.8 ml of the anesthetic.

8. The electric syringe as claimed in claim 5, wherein the lock removing button is configured to be operated in accordance with the connection of the cartridge holder to the cartridge holder connecting part.

9. The electric syringe as claimed in claim 5 further comprising a biasing member configured to apply a biasing force to the push member,
wherein the push member is configured to move in a state contacted with the rubber plug of the cartridge in accordance with the connection of the cartridge holder to the cartridge holder connecting part, and
wherein the push member is configured to be in contact with the rubber plug at a constant pressure by the biasing force applied by the biasing member when the cartridge holder is connected to the cartridge holder connecting part.

10. The electric syringe as claimed in claim 1 further comprising:
a cartridge holder connecting part; and
a cartridge holder configured to hold the cartridge and configured to be connectable to the cartridge holder connecting part.

11. The electric syringe as claimed in claim 10, wherein the cartridge holder is configured to hold one of a plurality of cartridges having different lengths, and configured to be connectable to the cartridge holder connecting part.

12. The electric syringe as claimed in claim 11, wherein the cartridge holder is configured to hold one of a first cartridge filled with 1.0 ml of the anesthetic and a second cartridge filled with 1.8 ml of the anesthetic.

13. The electric syringe as claimed in claim 1, further comprising a cartridge holder connecting part configured to be connected with a cartridge holder configured to hold the cartridge and having a groove on an outer peripheral surface thereof,
wherein the cartridge holder connecting part comprises:
a connecting ring having a tube body formed in a rotary body shape;
a ball pusher biasing member arranged in the tube body of the connecting ring;
a ball pusher arranged in the tube body of the connecting ring, applied with a biasing force by the ball pusher biasing member in the opposite direction to a connection direction of the cartridge holder, and formed in a cylindrical body shape having a multi-stage-shaped outer peripheral surface;
a mounting and removing ring biasing member arranged outside of the tube body of the connecting ring;
a mounting and removing ring arranged outside the tube body of the connecting ring, applied with a biasing force by the mounting and removing ring biasing member in the opposite direction to the connection direction of the cartridge holder, and formed in a cylindrical body shape having an inner peripheral surface with a groove;
a first ball arranged in the connecting ring in a manner to be movable between the multi-stage-shaped outer peripheral surface of the ball pusher and the grooved inner peripheral surface of the mounting and removing ring; and
a second ball arranged in the connecting ring in a manner to be movable between the grooved outer peripheral surface of the cartridge holder and the grooved inner peripheral surface of the mounting and removing ring,
wherein when the cartridge holder is connected, the cartridge holder presses against the ball pusher and thus the cartridge holder and the ball pusher are moved in linking with each other to thereby move the first ball to the ball pusher side and the second ball to the cartridge holder side, and
wherein when the cartridge holder is connected, the mounting and removing ring released from the movement restraint by the first ball is moved in the opposite direction to the cartridge insertion direction to press against the first and second balls, thereby connecting the cartridge holder to the cartridge holder connecting part.

14. The electric syringe as claimed in claim 1 further comprising:
a cartridge holder connecting part; and
a cartridge holder configured to hold one of a plurality of cartridges having different lengths, and configured to be connectable to the cartridge holder connecting part.

15. The electric syringe as claimed in claim 14, wherein the cartridge holder is configured to hold one of a first cartridge filled with 1.0 ml of the anesthetic and a second cartridge filled with 1.8 ml of the anesthetic.

16. The electric syringe as claimed in claim 1, wherein the control unit controls the drive motor to move the push member to reach a selected one of a plurality of selectable injection speeds by linearly increasing the injection speed of the anesthetic at the constant, predetermined rate at the beginning of the injection and until reaching the selected injection speed.

17. The electric syringe as claimed in claim 16, wherein the plurality of selectable injection speeds includes speeds of 0.005 mL/sec, 0.011 mL/sec and 0.016 mL/sec.

18. An electric syringe for injecting a dental anesthetic by pressing a rubber plug of a cartridge filled with an anesthetic, thereby injecting the anesthetic from a needlepoint of a dental needle connected to the cartridge, the electric syringe comprising:
- a push member configured to press and move the rubber plug of the cartridge;
- a drive motor configured to generate a drive force;
- a transmission mechanism part configured to transmit the drive force to the push member;
- an operation switch having a window hole portion and a sensor of a light reflection type which detects whether or not the window hole portion is closed;
- a control unit configured to control a moving of the push member by controlling the drive motor,
- wherein the control unit starts the injection of the anesthetic when the sensor of the operation switch detects that the window hole portion is closed and controls the drive motor to move the push member to linearly increase an injection speed of the anesthetic at a constant, predetermined rate at the beginning of the injection and until reaching a selected injection speed, and then to move the push member to inject the anesthetic at the selected injection speed without further increase; and
- a sound output unit configured to output a buzzing or melodic sound,
- wherein the control unit controls the sound output unit to output the sound during the injection of the anesthetic.

19. An electric syringe for injecting a dental anesthetic by pressing a rubber plug of a cartridge filled with an anesthetic, thereby injecting the anesthetic from a needlepoint of a dental needle connected to the cartridge, the electric syringe comprising:
- a push member configured to press and move the rubber plug of the cartridge;
- a drive motor configured to generate a drive force;
- a transmission mechanism part configured to transmit the drive force to the push member;
- a control unit configured to control a moving of the push member by controlling the drive motor,
- wherein the control unit controls the drive motor to move the push member to gradually increase an injection speed of the anesthetic in the beginning of the injection and to move the push member to inject the anesthetic in a constant injection speed after a predetermined time has elapsed; and
- an operation switch having a window hole portion and a sensor of a light reflection type in which detects whether or not the window hole portion is closed,
- wherein the control unit starts the injection of the anesthetic when the sensor of the operation switch detects that the window hole portion is closed.

20. An electric syringe for injecting a dental anesthetic by pressing a rubber plug of a cartridge filled with an anesthetic, thereby injecting the anesthetic from a needlepoint of a dental needle connected to the cartridge, the electric syringe comprising:
- a push member configured to press and move the rubber plug of the cartridge;
- a drive motor configured to generate a drive force;
- a transmission mechanism part configured to transmit the drive force to the push member, comprising:
- a lock removing button arranged on a cover case of the electric syringe; and
- a clutch mechanism portion configured to release the transmission of the drive force when the lock removing button is operated; and
- a control unit configured to control a moving of the push member by controlling the drive motor,
- wherein the control unit controls the drive motor to move the push member to gradually increase an injection speed of the anesthetic in the beginning of the injection and to move the push member to inject the anesthetic in a constant injection speed after a predetermined time has elapsed.

* * * * *